(12) United States Patent
Lewis

(10) Patent No.: US 11,925,515 B2
(45) Date of Patent: Mar. 12, 2024

(54) THROMBECTOMY DEVICE CLEANING APPARATUS

(71) Applicant: Karyn Lewis, Spring, TX (US)

(72) Inventor: Karyn Lewis, Spring, TX (US)

( * ) Notice: Subject to any disclaimer, the term of this patent is extended or adjusted under 35 U.S.C. 154(b) by 784 days.

(21) Appl. No.: 16/952,169

(22) Filed: Nov. 19, 2020

(65) Prior Publication Data

US 2022/0151729 A1     May 19, 2022

(51) Int. Cl.
*A61B 90/70*     (2016.01)

(52) U.S. Cl.
CPC ........ *A61B 90/70* (2016.02); *A61B 2090/701* (2016.02)

(58) Field of Classification Search
CPC ... A61B 1/122; A61B 17/22031; A61B 17/22; A61B 50/30; A61B 2090/701; A61B 90/70; A61C 15/00–048; A61C 19/002; B08B 3/047; B08B 9/023; A61M 39/16; A46B 2200/3013; A46B 2200/40; A46B 2200/3073; A46B 13/001
USPC ........................ 132/322, 324–327; 15/104.04
See application file for complete search history.

(56) References Cited

U.S. PATENT DOCUMENTS

| | | |
|---|---|---|
| 3,972,812 A | 8/1976 | Gresl, Jr. |
| D317,570 S | 6/1991 | Kryk |
| 5,059,319 A | 10/1991 | Welsh |
| 5,722,964 A | 3/1998 | Herweck |
| 5,824,126 A | 10/1998 | Chen |
| 5,855,774 A | 1/1999 | Boelter |
| 6,263,781 B1 | 7/2001 | Calagui |
| 6,280,429 B1 | 8/2001 | Lewis |
| 2015/0305575 A1* | 10/2015 | Chihi ........................ A47K 5/03 206/77.1 |

FOREIGN PATENT DOCUMENTS

| | | | | |
|---|---|---|---|---|
| CN | 2129288 Y | * | 4/1993 | |
| WO | WO9932170 | | 7/1999 | |
| WO | WO-2014076615 A2 | * | 5/2014 | ............ A61M 25/00 |

OTHER PUBLICATIONS

Machine Translation of CN-2129288-Y (Year: 1993).*

* cited by examiner

*Primary Examiner* — Eric J Rosen
*Assistant Examiner* — Robert C Moore

(57) ABSTRACT

A thrombectomy device cleaning apparatus for cleaning a thrombectomy device while maintaining the integrity of removed blood clots includes a box with a box left side and a box right side each having a receiving channel adjacent an open box top side. A mesh screen is coupled to a plurality of hinges. The mesh screen has a screen channel extending from a screen left edge to a screen right edge with a profile conforming to a receiving channel of each of the box left side and the box right side. The channel receives a thrombectomy device. A lid moves between a closed position covering the mesh screen in the use position and an open position exposing the mesh screen. A pair of brush rollers is coupled to the lid and positioned to rest within the screen channel of the mesh screen. The pair of brush receives the thrombectomy device therebetween.

8 Claims, 5 Drawing Sheets

THROMBECTOMY DEVICE CLEANING APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to medical cleaning devices and more particularly pertains to a new medical cleaning device for cleaning a thrombectomy device while maintaining the integrity of removed blood clots.

(2) Description of Related Art Including Information Disclosed Under 37 CFR 1.97 and 1.98

The prior art relates to medical cleaning devices. Known devices utilize a variety of filtration mechanisms. These devices, however, are not designed to clean a thrombectomy device and lack a grooved mesh screen to receive said device. Known devices also lack brush rollers for cleaning and an absorptive pad to collect water utilized in the cleaning process.

BRIEF SUMMARY OF THE INVENTION

An embodiment of the disclosure meets the needs presented above by generally comprising a box having a box left side, a box right side, a box front side, a box back side, a box bottom side, and an open box top side. The box left side and the box right side each have a receiving channel adjacent the box top side. A plurality of hinges is coupled to the box. The plurality of hinges is coupled to the box back side adjacent the box top side. A mesh screen is coupled to the plurality of hinges. The mesh screen hingingly moves between a use position covering the open box top side and a stored position. The mesh screen has a screen channel extending from a screen left edge to a screen right edge. The channel has a profile conforming to the receiving channel of each of the box left side and the box right side. The channel is configured to receive a thrombectomy device. A lid is coupled to the plurality of hinges. The lid hingingly moves between a closed position covering the mesh screen in the use position and an open position exposing the mesh screen. A pair of brush rollers is coupled to the lid. The pair of brush rollers is coupled to a lid bottom side of the lid and is positioned to rest within the screen channel of the mesh screen. The pair of brush rollers is configured to receive the thrombectomy device therebetween.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
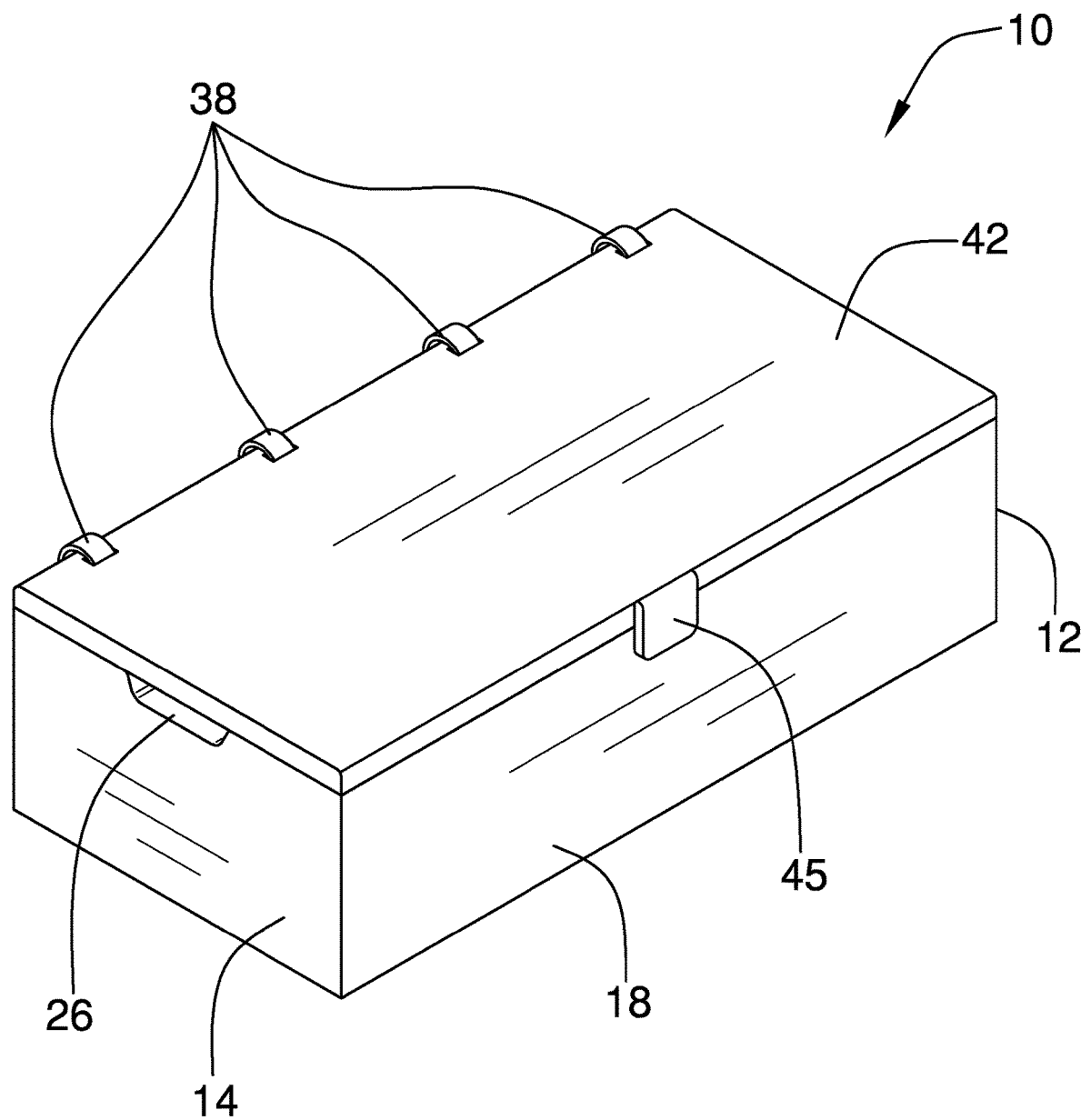
FIG. 1 is an isometric view of a thrombectomy device cleaning apparatus according to an embodiment of the disclosure.

With reference now to the drawings, and in particular to FIGS. 1 through 5 thereof, a new medical cleaning device embodying the principles and concepts of an embodiment of the disclosure and generally designated by the reference numeral 10 will be described.

As best illustrated in FIGS. 1 through 5, the thrombectomy device cleaning apparatus 10 generally comprises a box 12 having a box left side 14, a box right side 16, a box front side 18, a box back side 20, a box bottom side 22, and an open box top side 24. The box left side 14 and the box right side 16 each have a receiving channel 26 adjacent the box top side 24. Each receiving channel 26 may have a horizontal medial portion 28 and a pair of outer angled side portions 30. The box front side 18 may have a lip 32 extending within the box 12 adjacent the box top side 24.

An absorbent pad 34 may be coupled to the box 12. The absorbent pad 34 is removably coupled to the box bottom side 22 within the box 12 to capture as much fluid as possible during use and then to be removed for cleaning and drying. The absorbent pad 34 may extend from the box left side 14 to the box right side 16. The box bottom side 22 may have a pair of inner rounded edges 36 adjacent the box front side 18 and the box back side 20 to facilitate the cleanup of fluid from within the box 12.

A plurality of hinges 38 is coupled to the box 12. The plurality of hinges 38 is coupled to the box back side 20 adjacent the box top side 24. Each of the plurality of hinges 38 may be circular in order to support both a mesh screen 40 and a lid 42. The mesh screen 40 hingingly moves between a use position covering the open box top side 24 shown in FIG. 3 and a stored position shown in FIG. 2. The mesh screen 40 has a screen channel 44 extending from a screen left edge 46 to a screen right edge 48. The screen channel 44 has a profile 50 conforming to the receiving channel 26 of each of the box left side and the box right side to accommodate the screen channel 44 when the mesh screen 40 is in the use position. The screen channel 44 is configured to receive a thrombectomy device 52. The mesh screen 40 rests on the lip 32 in the use position in order to be supported in parallel to the open box top side 24 without interfering with the lid 42.

Figure 2:
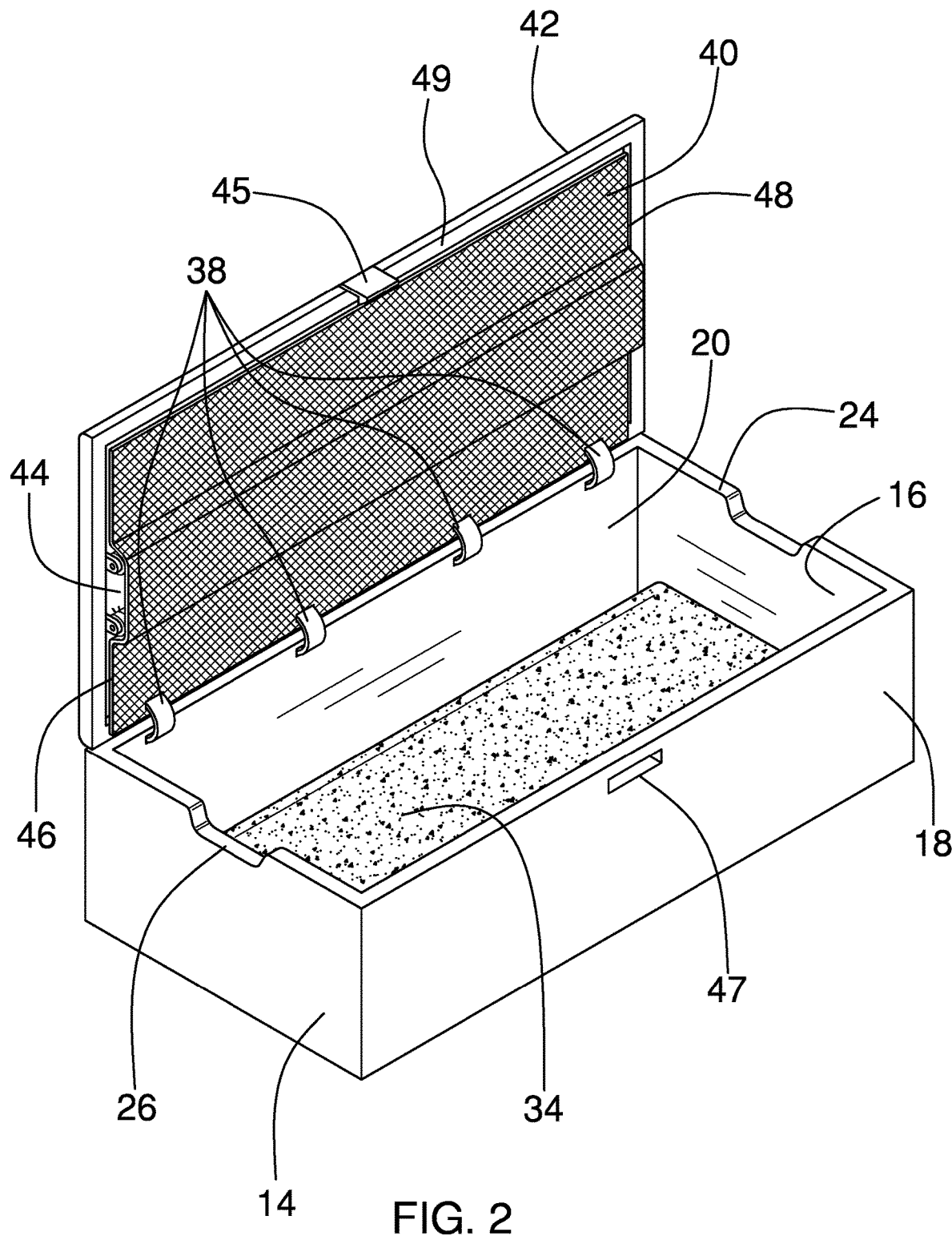
FIG. 2 is an isometric view of an embodiment of the disclosure.
Figure 3:
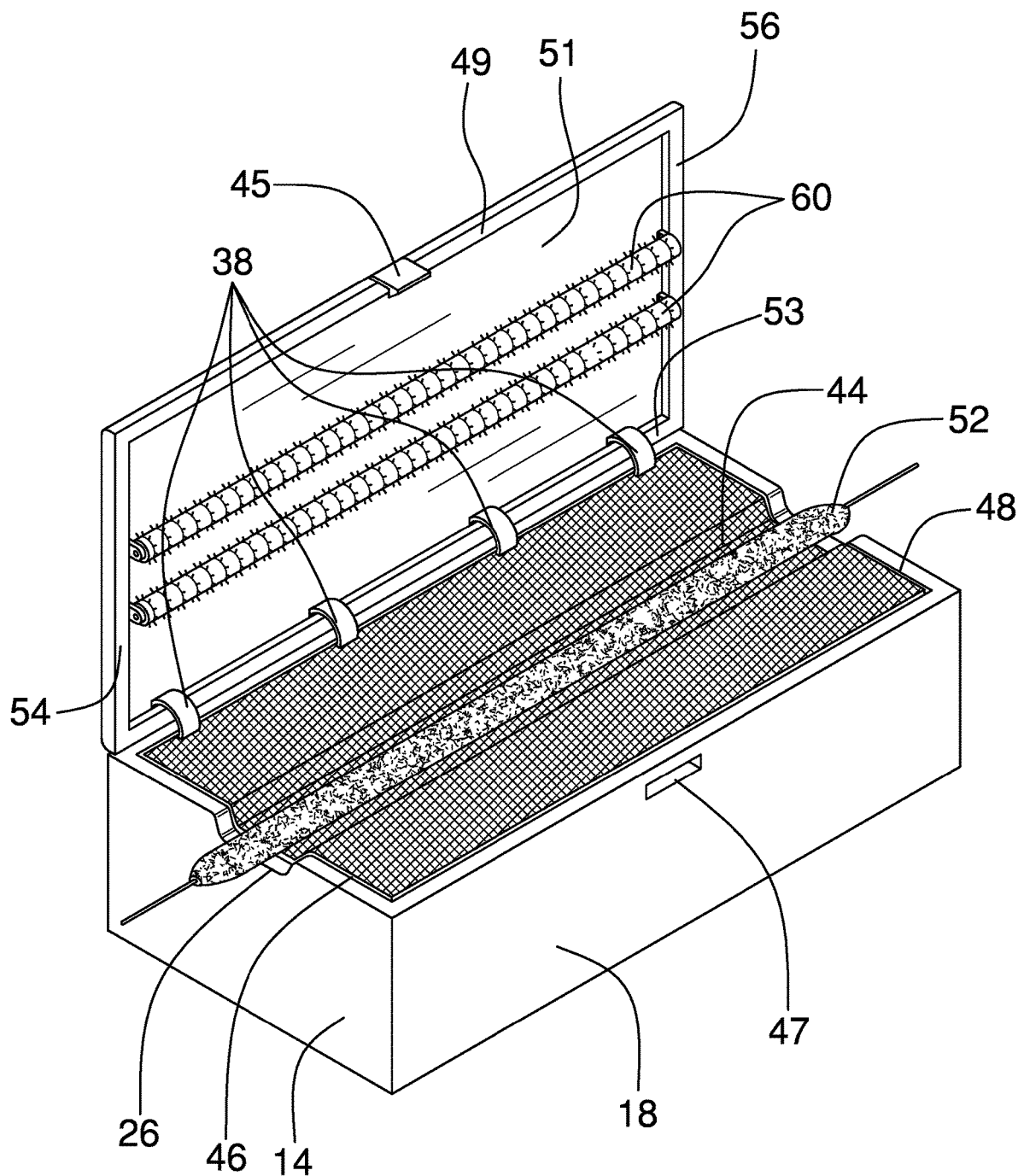
FIG. 3 is an isometric view of an embodiment of the disclosure.
Figure 4:
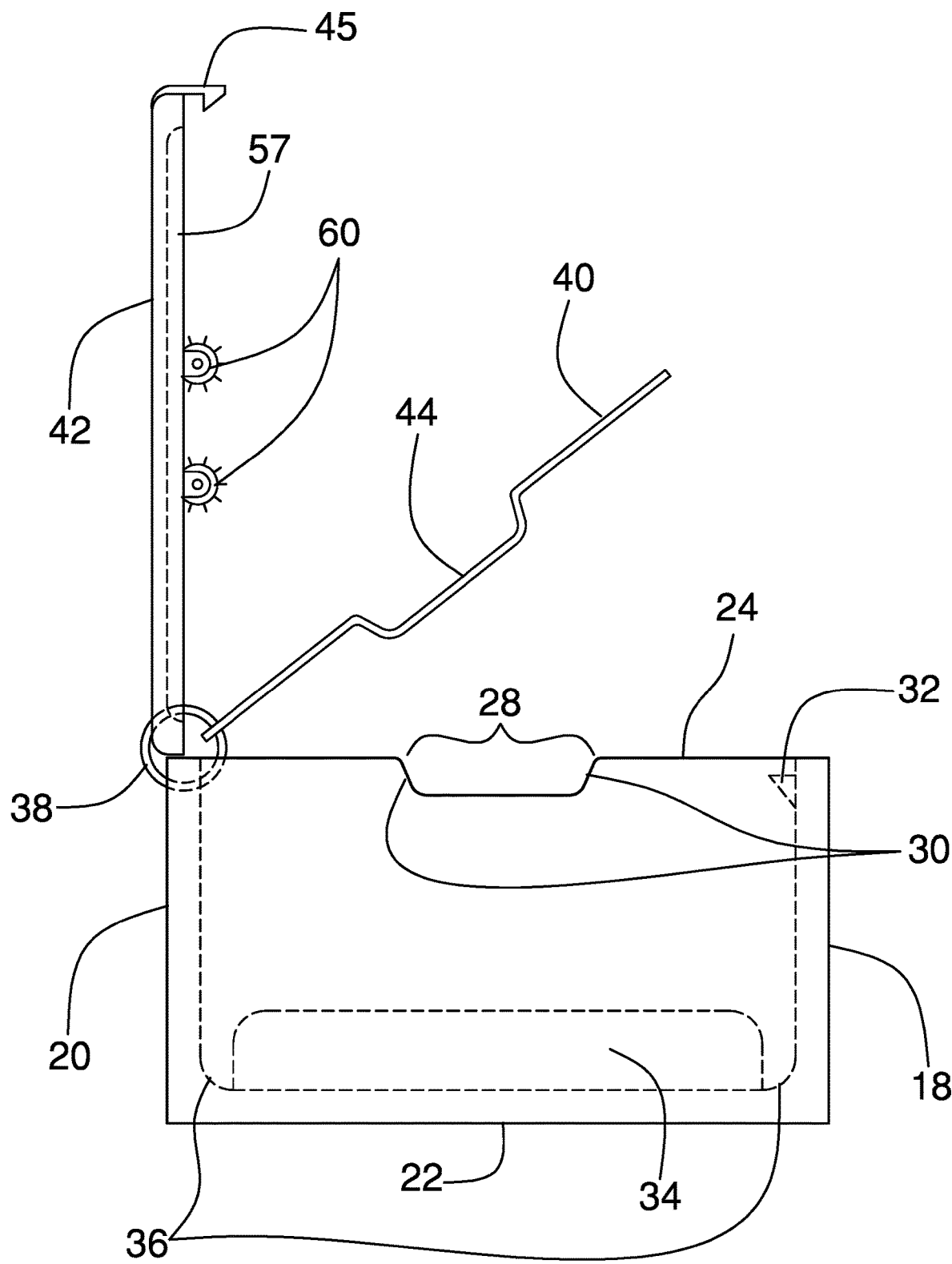
FIG. 4 is a side elevation view of an embodiment of the disclosure.
Figure 5:
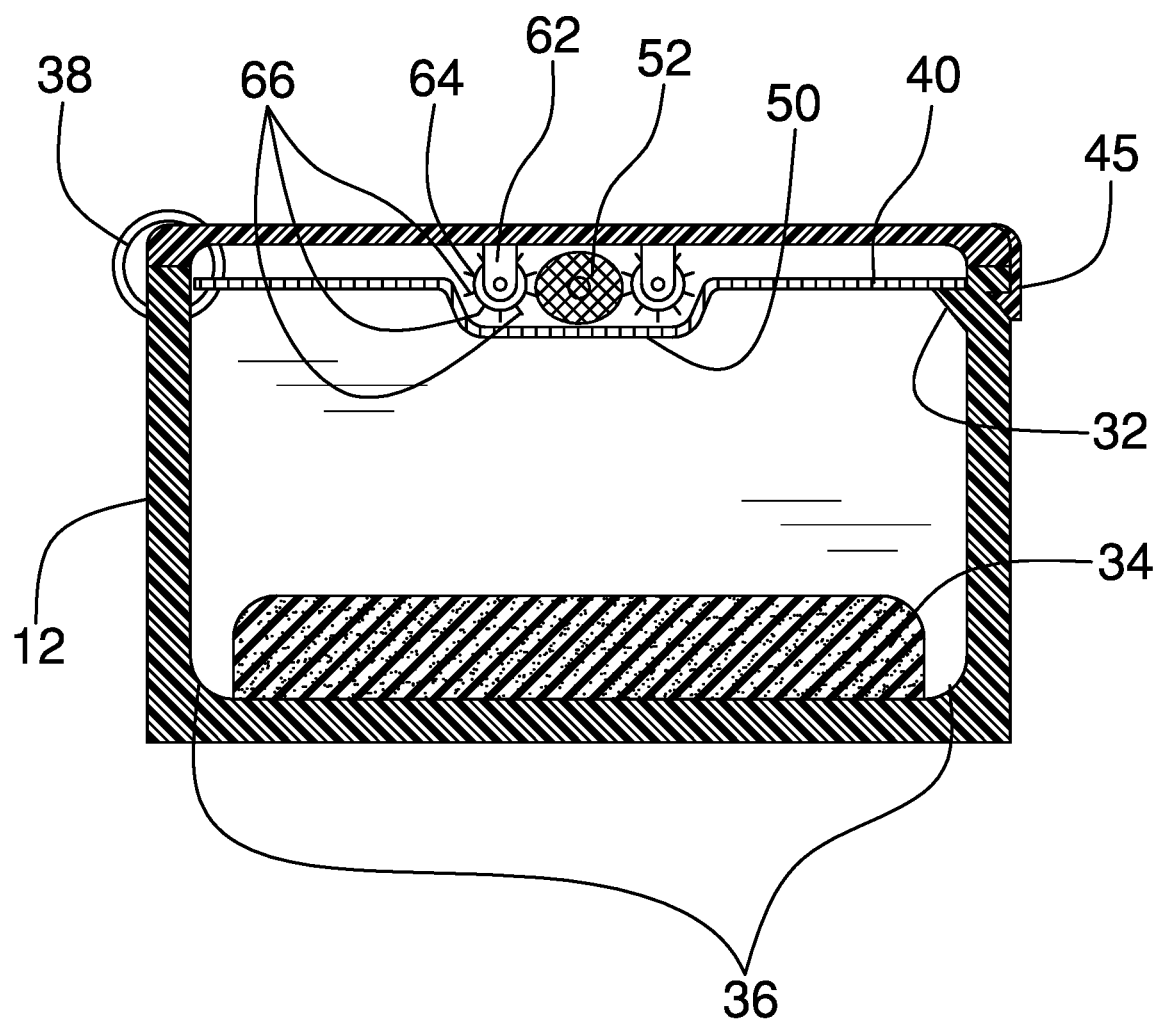
FIG. 5 is a cross-sectional view of an embodiment of the disclosure.

The lid 42 is coupled to the plurality of hinges 38 and hingingly moves between a closed position shown in FIG. 1 covering the mesh screen 40 in the use position and an open position shown in FIGS. 2 and 3 exposing the mesh screen 40. A latch 45 may be coupled to the lid 42. The box front side 18 may have a catch depression 47. The latch 44 is coupled to a lid front edge 49 of the lid and is selectively engageable with the catch depression 47 of the box front side to secure the lid 42 in the closed position. The lid front edge 49 may form a lid cavity 51 with a lid back edge 53, a lid left edge 54, a lid right edge 56, and a lid bottom side 58.

A pair of brush rollers 60 is coupled to the lid 42. The pair of brush rollers 60 is coupled to the lid bottom side 58 and is positioned to rest within the screen channel 44 of the mesh screen. The pair of brush rollers 60 is configured to receive the thrombectomy device 52 therebetween. Each of the brush rollers 60 may have a pair of ears 62 extending from the lid bottom side 58, a cylindrical roller body 64 rotatingly coupled between the pair of ears 62, and a plurality of bristles 66 extending from the roller body 64. The thrombectomy device 52 is contacted by the plurality of bristles 66 of each brush roller 60. The lid cavity 51 partially accommodates the brush rollers 60 to allow for rotation with minimal protrusion from the lid 42.

In use, the thrombectomy device 52 is placed within the screen channel 44 with the mesh screen 40 in the use position. Water may be poured over the thrombectomy device 52 for cleaning which is then absorbed by the absorbent pad 34 to minimize mess. The lid 42 is moved to the closed position to place the pair of brush rollers 60 on each side of the thrombectomy device 52 to allow for frictional cleaning. The plurality of bristles 66 of each brush roller 60 is sufficiently stiff to remove blood clots and plaque from the thrombectomy device 52 while maintaining the integrity of the blood clots and plaque.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A thrombectomy device cleaning apparatus comprising:
   a box having a box left side, a box right side, a box front side, a box back side, a box bottom side, and an open box top side, the box left side and the box right side each having a receiving channel adjacent the box top side;
   a plurality of hinges coupled to the box, the plurality of hinges being coupled to the box back side adjacent the box top side;
   a mesh screen coupled to the plurality of hinges, the mesh screen hingingly moving between a use position covering the open box top side and a stored position, the mesh screen having a screen channel extending from a screen left edge to a screen right edge, the screen channel having a profile conforming to the receiving channel of each of the box left side and the box right side, the screen channel being configured to receive a thrombectomy device;
   a lid coupled to the plurality of hinges, the lid hingingly moving between a closed position covering the mesh screen in the use position and an open position exposing the mesh screen; and
   a pair of brush rollers coupled to the lid, the pair of brush rollers being coupled to a lid bottom side of the lid and being positioned to rest within the screen channel of the mesh screen, the pair of brush rollers being configured to receive the thrombectomy device therebetween.

2. The thrombectomy device cleaning apparatus of claim 1 further comprising an absorbent pad coupled to the box, the absorbent pad being removably coupled to the box bottom side within the box.

3. The thrombectomy device cleaning apparatus of claim 1 further comprising the box bottom side having a pair of inner rounded edges adjacent the box front side and the box back side.

4. The thrombectomy device cleaning apparatus of claim 1 further comprising the box front side having a lip extending within the box adjacent the box top side; the mesh screen resting on the lip in the use position.

5. The thrombectomy device cleaning apparatus of claim 1 further comprising each of the plurality of hinges being circular.

6. The thrombectomy device cleaning apparatus of claim 1 further comprising the box front side having a catch depression; a latch being coupled to the lid, the latch being coupled to a lid front edge and being selectively engageable with the catch depression of the box front side to secure the lid in the closed position.

7. The thrombectomy device cleaning apparatus of claim 1 further comprising each of the brush rollers having a pair of ears extending from the lid bottom side, a cylindrical roller body rotatingly coupled between the pair of ears, and a plurality of bristles extending from the roller body.

8. A thrombectomy device cleaning apparatus comprising:
- a box having a box left side, a box right side, a box front side, a box back side, a box bottom side, and an open box top side, the box left side and the box right side each having a receiving channel adjacent the box top side, the box bottom side having a pair of inner rounded edges adjacent the box front side and the box back side, the box front side having a lip extending within the box adjacent the box top side, the box front side having a catch depression;
- an absorbent pad coupled to the box, the absorbent pad being removably coupled to the box bottom side within the box;
- a plurality of hinges coupled to the box, the plurality of hinges being coupled to the box back side adjacent the box top side, each of the plurality of hinges being circular;
- a mesh screen coupled to the plurality of hinges, the mesh screen hingingly moving between a use position covering the open box top side and a stored position, the mesh screen having a screen channel extending from a screen left edge to a screen right edge, the screen channel having a profile conforming to the receiving channel of each of the box left side and the box right side, the screen channel being configured to receive a thrombectomy device, the mesh screen resting on the lip in the use position;
- a lid coupled to the plurality of hinges, the lid hingingly moving between a closed position covering the mesh screen in the use position and an open position exposing the mesh screen;
- a latch being coupled to the lid, the latch being coupled to a lid front edge and being selectively engageable with the catch depression of the box front side to secure the lid in the closed position; and
- a pair of brush rollers coupled to the lid, the pair of brush rollers being coupled to a lid bottom side of the lid and being positioned to rest within the screen channel of the mesh screen, the pair of brush rollers being configured to receive the thrombectomy device therebetween, each of the brush rollers having a pair of ears extending from the lid bottom side, a cylindrical roller body rotatingly coupled between the pair of ears, and a plurality of bristles extending from the roller body.

\* \* \* \* \*